United States Patent [19]

Abe et al.

[11] Patent Number: 4,833,077

[45] Date of Patent: May 23, 1989

[54] METHOD FOR PRODUCING HUMAN ANTIBODY

[75] Inventors: Tsutomu Abe; Sagae Hiromitsu, both of Fuji, Japan

[73] Assignee: Asahi Kasei Kogyo Kabashiki Kaisha, Osaka, Japan

[21] Appl. No.: 750,199

[22] Filed: Jul. 1, 1985

Related U.S. Application Data

[63] Continuation of Ser. No. 501,136, Jun. 6, 1983, abandoned.

[30] Foreign Application Priority Data

Jun. 9, 1982 [JP] Japan .................................. 57-97596
Mar. 24, 1983 [JP] Japan .................................. 58-48011

[51] Int. Cl.⁴ ........................ C12P 21/00; C12N 5/00; C12N 15/00; C12R 1/91
[52] U.S. Cl. .................................. 435/68; 435/172.2; 435/240.27; 435/948; 935/100
[58] Field of Search .................. 435/68, 172.2, 240.27, 435/948; 436/548; 935/100

[56] References Cited

U.S. PATENT DOCUMENTS 4,271,145  6/1981  Wands et al. .......................... 424/85

FOREIGN PATENT DOCUMENTS 0028902  5/1981  European Pat. Off. .
0033579  8/1981  European Pat. Off. .
0044722  1/1982  European Pat. Off. ............ 436/548
0057107  8/1982  European Pat. Off. .
2086937  5/1982  United Kingdom ................ 436/548
2092614  8/1982  United Kingdom .
2102832  2/1983  United Kingdom .

OTHER PUBLICATIONS

Steinitz et al., Nature 269, pp. 420–422, (1977).
Huang et al., Journal of the National Cancer Institute, 43(5), pp. 1119–1128, (1969).

Primary Examiner—John E. Tarcza
Attorney, Agent, or Firm—Pennie & Edmonds

[57] ABSTRACT

A method of effectively producing antobodies by creating antibody-producing hybrid cell lines utilizing an established B cell line as a parent cell lines and fusing these B cells to normal, human antibody-producing cells. A preferred established B cell line for use in this invention consists of B cells characterized by the presence of immunoglobulin at their cell surface.

2 Claims, No Drawings

METHOD FOR PRODUCING HUMAN ANTIBODY

This is a continuation of application Ser. No. 501,136 filed on June 6, 1983, now abandoned.

TECHNICAL FIELD

This invention relates to a method of producing human antibody by fusing B cells from established cell lines with normal, human antibody-producing cells, thereby creating hybrid cells capable of both continuous growth in culture and production of human antibodies. The hybrid cells may furthermore secrete antibodies into their culture medium permitting the easy harvesting of these antibodies.

More particularly, the invention involves the use of parent B cell lines which can grow continuously in culture and whose constituent cells have cell surface immunoglobulin, especially IgM or IgA. The parent B cell lines suitable for use in the present invention may secrete such cells surface immunoglobulin into the culture medium and may be unable to grow in selective medium. The parent B cell lines are further characterized by their facilitation of hybrid formation.

BACKGROUND ART

In recent years, hybrid cells which can produce human antibody have been made by two methods, which can be classified basically as follows:

(1) Producing hybrid cells by combining human antibody-producing cells with a myeloma cell line originally derived from mice, rats, or other rodents.

(2) Producing hybrid cells using a human myeloma cell line.

In the interspecific hybrid cells produced according to the first method, human chromosomes rapidly disappear; it is therefore extremely difficult to obtain stable human antibody-producing hybrid cell lines. In the second method, human myeloma cell lines die immediately in a polyethylene glycol solution, which is the most easily employed cell fusion agent, and thus, no hybrid cell line can be efficiently obtained.

DISCLOSURE OF THE INVENTION

The present inventors have found that by using an established human B cell line, comprising B cells having immunoglobulin at the cell surface, as one of the parent lines to form hybrid cells, cytotoxic effects due to cell fusion agents, such as polyethylene glycol, are minimized and cell fusion can be facilitated. Such an established B cell line can then be successfully fused with a normal, human antibody-producing cell line resulting in a hybrid cell line producing human antibodies.

The present invention is direceted to a method for producing immunoglobulin derived from such hybrid cell line obtained by the cell fusion of normal, human antibody-producing cells with human B cells, having immunoglobulin at the cell surface and from an established cell line, i.e., one which is capable of continuous growth (hereinafter referred to as "B cell line").

In general, established B cell lines suitable for use in the present invention are capable of growth in suspension and can be identified as having at least complement $C_3$ receptor, IgG Fc receptor, surface immunoglobulin, or the like, at the surface of the cell membrane. The present inventors have found that where such B cell lines, having at least one type of immunoglobulin at the cell surface, are fused to an antibody-producing cell line, antibodies are secreted efficiently by the hybrids.

The B cell lines which are employed in accordance with the present invention differ from human myeloma cell lines in that the former have immunoglobulin at the cell surface. Cytomorphologically, many more mucrones are present at the surface of B cell lines and therefore the agglutination property of these cell strains is stronger than other known cell strains.

Preferred examples of the B cell lines employed in the present invention are those in which secretion of immunoglobulin from B cell lines into the growth medium can be confirmed. The presence of immunoglobulin in the supernatant of the medium can be tested by known enzyme immunoassay methods or other known assay methods. By utilizing B cell lines secreting immunoglobulin as one parent cell line, this secretory function would also be effectively expressed in the resultant hybrid cells; therefore, the production of antibodies derived from the normal, human antibody-producing parent cells would be accelerated.

It is preferred that immunoglobulin present at the surface of the B cell lines be of IgM or IgA type. In a preferred embodiment of this invention, B cell lines secrete IgM or IgA type immunoglobulin into the culture medium. By the use of such B cell lines as the parent line, IgG type antibody, coded by a normal, antibody-producing parent cell and which would be the primary immunoglobulin produced by hybrid cells, can be easily detected.

For the purpose of this invention, it is preferred that the average number of chromosomes in the parent B cell line be from 40 to 50 to approximate as closely as possible the 46 chromosomes present in a normal human diploid cell.

The time required for two-fold multiplication in a logarithmic growth phase of the B cell lines to be used in this invention should be short, preferably in the range of 12 to 36 hours.

Cell lines in which the growth rate is decreased due to mycoplasma infection or other contaminants are normally not suited for use in the present invention.

Examples of the B cell lines which are employed in accordance with the present invention include RPMI-1788 described in *Journal of the National Cancer Institute*, 43, 1119–1128 (1967), a derivative of RPMI-1788, (ATCC Deposit No. CRL 8118), IM-9 (ATCC Deposit No. CCL 159) described in *Proceedings of the National Academy of Sciences*, 71, 84–88 (1974), 64–10 described in *International Journal of Cancer*, 6 426–449 (1970), Bristol-7, and GM 1056A and GM 923 described in G. J. Haemmerling, V. Haemmerling and J. F. Kearney, "Monoclonal Antibodies and T Cell Hydridomas", pp. 432–444 (Elsevier/North-Holland Biochemical Press, Amsterdam 1981).

Of these B cell lines, RPMI-1788 and ATCC CRL 8118 which are IgM type antibody-producing cells and GM 1056A and GM 923 which are IgA type antibody-producing cells are particularly preferred since IgG type antibody produced by hybrid cells can be easily distinguished.

B cell lines suitable for use in the present invention can be constructed by in vitro cultivation of peripheral blood lymphocytes for long periods of time or by Epstein-Barr virus tranformation.

The B-cell lines described herein for use in this invention are resistant to cytotoxic effects from and even to contact with the cell fusion agent polyethylene glycol.

Consequently, they form hybrid cells more efficiently than the human myeloma cell lines previously used in the art.

There is no particular limitation to the basic composition of the medium used for cultivation of the B cell lines, but RPMI-1640 medium containing 10 to 20% fetal calf serum is ordinarily used.

The normal, human antibody-producing cells which are employed in the present invention are widely distributed in the body and include lymphocytes from peripheral blood, lymph nodes and spleen. There is no particular restriction as to the source of normal, human antibody-producing cells, but peripheral blood lymphocytes are usually employed since they can be obtained easily and non-invasively.

Cell fusion is effected by mixing B and antibody-producing cells to be fused at ordinary ambient temperature in the presence of cell fusion agents. Cell fusion can be mediated by various agents; polyethylene glycol solution and inactivated Sendai virus are two known methods. While there is no limitation as to the cell fusion method employed to practice the present invention, polyethylene glycol solution is recommended since its preparation and use are simple.

After completion of cell fusion, normal, human antibody- producing cells which are not fused gradually die and do not pose an obstacle to creating hybrid cell lines; however, B cells from an established B cell line, that are not fused, do not die and must be separated from the newly created hybrid cells.

Hybrid cells can be separated from B cells that are not fused by comparing properties among respective colonies, after colonies have been cloned in soft agar or by limiting dilution method. An easier separation technique is to employ an enzyme-deficient B cell line, which is unable to grow in selective medium, as the parent B cell line. An example of selective medium is HAT medium containing hypoxanthine, aminopterin and thymidine. HAT medium permits the proliferation of hybrid cells and prevents growth of unfused B cells which normally would continue to divide indefinitely. Aminopterin blocks de novo purine and pyrimidine synthesis by inhibiting the production of tetrahydrofolate. The addition of thymidine bypasses the block in pyrimidine synthesis, while hypoxanthine is included in the medium so that inhibited cells can synthesize purines using the nucleotide salvage pathway. The B cell line employed are mutants deficient or lacking hypoxanthine guanine phosphoribosyl transferase (HG PRT), or alternatively lacking thymidine kinase (TK), and thus cannot utilize the salvage pathways. In the surviving hybrids, the normal, human antibody-producing cells supply genetic information for production of this enzyme. As discussed above, since the normal, human antibody- producing cells themselves have a limited life span in culture, the only cells which can proliferate in HAT medium are hybrids formed between B and human antibody-producing cells.

Hypoxanthine guanine phosphoribosyl transferase deficient B cell line can be isolated by selecting a cell line capable of growth in a medium containing 8-azaguanine or 6-thioguanine; likewise, thymidine kinase deficient B cell line will be resistant to 5-bromo-deoxyuridine and can be recognized by their ability to grow in medium containing BUDR. The use of HAT medium is a well known method for selecting hybrid cells formed between cells from two different cell lines as described in "Science", vol. 145, 709–710 (1964).

to obtain an enzyme deficient cell line to be used in connection with present invention, the drug concentration necessary to supply selective pressure varies depending upon the drug sensitivities of the B cell line employed. Accordingly, the B cell line to be subjected to selective pressure is first cultivated in medium containing a range of drug concentrations in order to determine what concentration will lead to a growth rate one-half of the growth rate in drug-free medium. Starting with the drug concentration that halves the growth rate, the drug concentration is gradually increased 20–100 fold over the course of 2 to 6 months until an enzyme deficient B cell line is thereby acquired.

A preferred enzyme deficient B cell line is ATCC Deposit No. CRL 8118. CRL 8118 was originally isolated by applying selective pressure to RPMI-1788, a B cell line secreting IgM type immunoglobulin, by culturation in a medium containing 8-azaguanine. The cell line has an average chromosome number of 45, has a doubling time of 18 hours in logarithmic growth phase, possesses IgM type immunolobulin at the cell surface and secretes this IgM type immunoglobulin into the supernatant of the culture. This cell line fuses with normal, human antibody-producing cells with excellent efficiency.

The cell fusion process used to practice this invention is described generally as follows. Normal, human antibody-producing cells from peripheral blood is diluted three-fold with physiological saline, layered on top of a Ficoll-Conray solution gradient, and subjected to centrifugation at 400 G for 30 minutes. The peripheral blood lymphocyte fraction will appear as intermediate layer and is employed as the normal, human antibody-producing cell line.

To obtain normal, human antibody-producing cells, lymphocytes, from tissues such as the spleen or lymph nodes, the tissue used is first minced into small pieces and strained through a stainless steel mesh, thereby separating lymphocytes from other solid matter. Contaminating erythrocytes can be removed by hemolysis treatment utilizing a 0.14 M ammonium chloride solution or other known methods.

A suspension of the thus isolated normal, human antibody-producing cells are mixed together with a selected enzyme deficient B cell line, and the resulting mixture is centrifuged to remove completely the protein contaminants from the medium. There is no fixed ratio of the number of cells from the B cell line and the number of lymphocytes to be mixed together. The ratio chosen can range from 1:1 to a 100-fold excess of either cell type.

An agent promoting cell fusion between the two parent cell lines can now be added. For example, the cell fusion agent polyethylene glycol, molecular weight 1500–6000 can be diluted in protein-free growth medium or in Hanks' balanced salt solution (hereinafter referred to as Hanks' BSS) to make up a 35–55% solution. The resulting polyethylene glycol solution is added to the cell mixture dropwise slowly to make up a dose of 0.1 to 1.0 ml per $10^7$ cells. After standing for three minutes, the mixture is washed with protein-free growth medium to sufficiently dilute the polyethyene glycol.

The cells are then dispersed into HAT selective medium or other appropriate selective medium. The minimum concentration of aminopterin needed in HAT medium would be the amount required to completely kill the HG PRT or TK deficient parent B cell line; the maximum concentration can be as high as one hundred times the minimum concentration. The concentration of hypoxanthine and thymidine is not restricted, as long as no cytotoxic effects are observed, however the preferred concentration of hypoxanthine is approximately $10^{-4}$ M and of thymidine is approximately $1.5 \times 10^{-5}$ M.

The cell fusion mixture is next dispersed into 96-well microtiter tissue culture plates containing HAT or other selective growth medium. The cell mixture is sufficiently diluted to allow individual clones of hybrid cells to grow. These microtiter plates are then placed in a $CO_2$ incubator.

Individual hybrid colonies can be easily screened by any well-known immunological technique to detect secretion of the IgG type antibody coded by the human antibody-producing parent cell line into the supernatant of the culture medium. Since the preferred B cell parent lines possess and secrete either IgM or IgA type immunologlobulin, any IgG type antibody produced by hybrid cells will be easily detected. Screening of the hybrid cells to isolate those cells producing the desired antibody is thereby simplified, giving the present invention an advantage over methods known in the prior art.

Once a hybrid cell line, producing only one antibody having a specific antigenic specificity, has been isolated and purified, that particular cell line can be further cultivated and the antibody can be harvested directly from the supernatant of the culture medium. Alternatively, the desired hybrid cell line can be transplanted and grown in the peritoneal cavity of immuno-suppressed mammals. One example of a preferred host is a nude mouse strain whose thymus activity is depressed.

The advantages of utilizing a B cell line as one of the parent cell lines to form human antibody-producing hybrid cells according to the present invention include the following:

1. cytotoxicity after contact with a 45% polyethylene glycol solution for 10 minutes is less than that displayed by myeloma cells subjected to the same treatment;
2. isolation and multiplication of hybrid cells is simple; and
3. the antibody-producing capability of normal human antibody-producing cells can easily be transferred to the hybrid cell lines and secretion of IgG into the supernatant is facilitated.

It is apparent that many modifications and variations of this invention as described herein can be made without departing from the spirit and scope of the invention. The specific embodiments set forth below are intended to illustrate, without limitation, the features and advantages of the invention.

BEST MADE FOR CARRYING OUT THE INVENTION

EXAMPLE I

Selection of HG PRT Deficient B Cell Lines from Human B Lymphocyte-Derived Cell Line RPMI-1788

RPMI-1788 cells were grown to a concentration of $10^8$ cells in RPMI-1640 medium containing 10% fetal calf serum, then 1 mg/ml of 8-azaguanine was added to the medium. After confirming that the cell growth rate dropped to one-half of the rate in drug-free medium, discrete, viable cell clusters were individually captured with a micropipette while viewed under an inverted microscope. Each cell cluster was then diluted into tissue culture plate wells, filled with medium containing 8-azaguanine at one of the following concentration: 3 $\mu$g/ml, 10 $\mu$g/ml, and 20 $\mu$g/ml. After 15 days of cultivation, 24 different viable cells clusters (presumptive clones) were obtained. Cells from each of these 24 cell clusters were replicated into new wells and cultured in RPMI-1640 medium containing various concentrations of aminopterian plus 10% fetal calf serum. 3 out of 24 cell clusters were not viable following 15 days of cultivation in medium containing $4 \times 10^{-8}$M aminopterin. These 3 cell lines were presumed to be HG PRT deficient and that the minimum concentration of aminopterin required to kill these cell lines was $4 \times 10^{-8}$M. A presumptive HG PRT deficient cell cluster was diluted, dispersed, and then cultured to obtain a cell cluster assumed to be derived from one cell. This purified cell line was confirmed to have the above-described aminopterin sensitivity. This cluster was chosen for subsequent cell fusion experiments and was deposited in the American Type Culture Collection as ATCC CRL 8118.

Tolerance of ATCC CRL 8118 to Polyethylene Glycol

The tolerance of ATCC CRL 8118 to polyethylene glycol was determined in the following manner. Prior to the experiment, the proportion of viable CRL 8118 was determined by trypan blue dye exclusion. 97% of the cells were viable. Polyethylene glycol, M.W. 2000, was diluted in Hanks' BSS to make 2 ml of a 45% solution. After adjusting the pH of the solution to 8.2, bacteria were removed by filtration. This polyethylene glycol solution was gradually added dropwise to $2 \times 10^7$ CRL 8118 cells which previously had been throughly washed with Hanks' BSS for 2 minutes and 30 seconds. Thereafter, the cells in polyethylene glycol solution were incubated at 37° C. for 1 minute. Polyethylene glycol-treated cell solution was then slowly diluted with 20 ml of protein-free RPMI-1640 medium. The cell suspension was mildly centrifuged and resuspended in fresh RPMI-1640 medium containing 10% fetal calf serum. A quantity ($10^5$) of polyethythene glycol-treated cells suspended in fresh medium were inoculated into a 24 well tissue culture plate and incubated in a 5% $CO_2$ incubator at 37° C. for 3 days. The viable rate of the cell line was then measured by the method described above and determined to be 92%.

Cell Fusion

Using heparin as an anticoagulant, 20 ml of peripheral blood was collected from a normal volunteer. A suspension containing $2 \times 10^7$ fresh lymphocytes was obtained by a specific gravity centrifugation method using a Ficoll-Conray solution (specific gravity of 1.077).

The lymphocytes were then mixed with a corresponding number of CRL 8118 cells, centrifuged and resuspended in Hanks' BSS. After washing in Hanks' BSS three times, the cells were centrifuged and the Hanks' BSS poured off. As a cell fusion agent, 2 ml of a solution containing 45% of polyethylene glycol, M.W. 2000, diluted in Hanks' BSS was prepared, as a cell fusion agent. After adjusting the pH of this solution to 8.2, bacteria were removed by filtration. The polyethylene glycol solution was added dropwise slowly to the above-described mixture of washed cells over a time period of 2 minutes and 30 seconds, and then allowed to stand for 1 minute at 37° C.

Subsequently, the cells in polyethylene glycol solution were gradually diluted with 20 ml of protein-free RPMI-1640 medium. The diluted cell suspension was centrifuged gently, the supernatant decanted, and resuspended in 80 ml of a medium containing $10^{-7}$M of aminopterin, $10^{-4}$M of hypoxanthine and $1.5 \times 10^{-5}$M of thymidine.

200 ml of the fused cell suspended in HAT medium were poured in each well of 4 microtiter plates (96 wells/plate). Half of the growth medium was replaced by a fresh HAT medium every four days. Multiplication of cell clusters was observed after 20 days through an inverted microscope. Human IgG antibody in the culture supernatant was assayed by enzyme immunoassay using peroxidase-conjugated antiglobulin, and it was confirmed that human IgG was released in 78% of the culture wells.

EXAMPLE 2

Human B cell-derived, IgG-secreting cell line, Bristol-7 was subjected to selective presure of 8-azaguanine-containing medium as in Example 1 in order to isolate a HG PRT deficient line.

The sensitivity of the HG PRT deficient B cell line to polyethylene glycol was measured in the manner described in Example 1. The viable rate was 94% prior to sensitivity testing, whereas, after treating with polyethylene glycol, and cultivation for 3 days, the viable rate was 88%.

Next, cell fusion with lymphocytes collected from a normal volunteer was performed in a manner similar to Example 1. After incubation for 20 days, it was confirmed that human IgM was released in 32% of the culture well.

EXAMPLE 3

Selection of HG PRT Deficient Line from Human B Cell-Derived Cell Line GM 1056A

GM 1056 cells were grown to a concentration of $10^8$ cells in RPMI-1640 medium containing 10% fetal calf serum. 1 mg/ml of 6-thioguanine was then added, and incubation was continued for 10 days. As explained in Example 1, a viable cell cluster from the 6-thioguanine treated medium is diluted into medium containing respectively 2 μg/ml, 5 μg/ml, 10 μg/ml, and 20 μg/ml of 6-thioguanine. After 15 more days of cultivation, 25 individual cell clusters were noted and their sensitivity to aminopterin was tested as described in Example 1. 2 out of 25 cell cultures dies in medium containing aminopterin and were therefore considered to be HG PRT deficient cell lines. Cells not exposed to aminopterin, from the same cell cluster that could not grow in HAT selective medium, were dispersed and recultured in order to obtain a cell line derived from one cell (clone). Sensitivity of this purified cell line to aminopherin was rechecked, and the cell line was named GM 1056A-TGR.

Tolerance of GM 1056A-TGR to Polyethylene Glycol

Prior to using GM 1056A-TGR for cell fusion, its tolerance to polyethylene glycol was tested in manner set forth in Example 1. 96% of the cells were viable prior to treatment. After treatment with polyethylene glycol solutions, washing, resuspension in fresh growth medium, and culturation for 3 days, 92% of the cells were viable.

Cell Fusion

GM 1056A-TGR was fused with peripheral blood lymphocytes collected from a normal volunteer by the method in Example 1. After the cell fusion step was carried out, cultivation of the cell mixture in selective medium was continued for 20 days, thereafter cell clusters which were viable and growing were noted under an inverted microscope. The presence of human IgG and IgA in the culture supernatant of the individual wells was analyzed by enzyme immunoassay using peroxidase-conjugated antibody. It was confirmed that IgG was produced in 76% of wells and human IgA in 34% of the wells.

Comparative Example

For a comparative example, the same series of procedures were performed using human myeloma cell line U-266 (Clinical Experimental Immunology, 7, 477–489 (1970)). As a first step HG PRT deficient cell line was isolated in a manner similar to Example 1.

The sensitivity of the myeloma line to polyethylene glycol was measured in a manner similar to Example 1. The viable rate was 93% prior to the experiment; the viable rate was only 23% after treatment with polyethylene glycol, washing, and continued incubating for 3 days.

Next, cell fusion with peripheral blood lymphocytes collected from a normal volunteer was carried out in the manner given to Example 1. After incubation for 20 days, viable cells were detected by an inverted microscope but not observable by the naked eye. Furthermore, IgG and IgM in the culture supernatant of the well were measured in a manner similar to Example 1 but were lower than the detection limit of 1 ng/ml.

The invention described and claimed herein is not to be limited in scope by the line deposited, as referred to in Example 1, since the deposited embodiment is intended as a single illustration of one aspect of the invention and any equivalent cell lines which will produce a functionally equivalent human antibody-producing hybrid cell lines are within the scope of this invention. Indeed, various modifications of the invention in addition to those shown and described herein will become apparent to those skilled in the art from the foregoing description. Such modifications are also intended to fall within the scope of the appended claims.

Having thus described our invention, what we claim as new and desire to secure by Letters Patent is:

1. A method for producing a human antibody by fusing a normal, human antibody-producing cell with the B cell line ATCC CRL 8118.

2. An antibody-secreting hybridoma produced by fusing a normal, human antibody-producing cell with the B cell line ATCC CRL 8118.

* * * * *